United States Patent [19]

Siddall

[11] 4,137,273

[45] Jan. 30, 1979

[54] PHENOLIC ETHERS

[75] Inventor: John B. Siddall, Palo Alto, Calif.

[73] Assignee: Zoecon Corporation, Palo Alto, Calif.

[21] Appl. No.: 324,903

[22] Filed: Jan. 19, 1973

Related U.S. Application Data

[63] Continuation of Ser. No. 100,787, Dec. 22, 1970, abandoned, which is a continuation-in-part of Ser. No. 59,762, Jul. 30, 1970, Pat. No. 3,709,914.

[51] Int. Cl.$^2$ ............................................. C07C 43/20
[52] U.S. Cl. ................................ 568/648; 260/606 F; 260/609 E; 260/609 F; 260/607 AR; 260/607 AL; 260/654 R; 568/644; 568/646; 568/654; 424/340
[58] Field of Search .......... 260/613 R, 611 A, 613 D, 260/612 D

[56] References Cited

U.S. PATENT DOCUMENTS

| | | | |
|---|---|---|---|
| 2,134,001 | 10/1938 | Mills et al. | 260/613 D |
| 2,838,572 | 6/1958 | Rigterink | 260/611 A |
| 2,875,251 | 2/1959 | Rigterink | 260/611 A |

OTHER PUBLICATIONS

Sarmiento et al., Science vol. 179, (1973) 1342–1343.
Bowers, Index Chemicus, vol. 33, Issue 293, 114,522.
Borkovic, Insect Chemosterilants (1966), 61–63.

*Primary Examiner*—Henry R. Jiles
*Assistant Examiner*—Robert T. Bond
*Attorney, Agent, or Firm*—Donald W. Erickson

[57] ABSTRACT

Novel phenyl derivatives of formula I useful for the control of insects and novel intermediates.

10 Claims, No Drawings

PHENOLIC ETHERS

This is a continuation of Ser. No. 100,787, filed Dec. 22, 1970, now abandoned, which is a continuation-in-part of Ser. No. 59,762, filed July 30, 1970, now U.S. Pat. No. 3,709,914.

This invention relates to novel phenyl derivatives, syntheses thereof and novel intermediates. The phenyl derivatives of this invention are represented by formula I below.

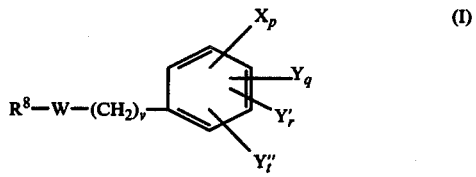

wherein,
$R^8$ is one of the groups A, B or C:

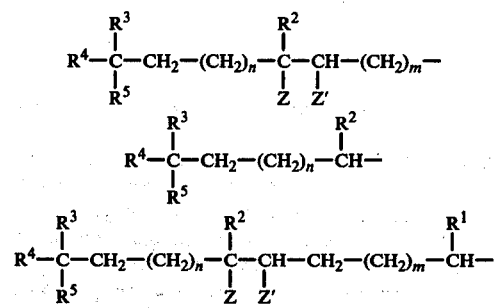

m is the positive integer one or two; n is the positive integer two or three; v is zero or the positive integer one; W is oxygen, sulfur, sulfinyl or sulfonyl; X is halo; Y is lower alkyl or lower alkoxy; Y' is nitro; Y" is nitroso, cyano, halomethyl, dihalomethyl, trihalomethyl, or the group $-R_s^9-SO_r-R^{10}$; p is zero or the positive integer one, two, three or four; q is zero or the positive integer one, two or three; r is zero or the positive integer one or two; s is zero or the positive integer one; t is zero or the positive integer one or two; at least one of q or t is a positive integer;

$R^9$ is alkylene of one to eight carbon atoms;
$R^{10}$ is lower alkyl, cycloalkyl or aralkyl;
each of $R^1$, $R^2$, $R^3$ and $R^4$ is lower alkyl;
$R^5$ is the group —OR in which R is hydrogen, lower alkyl, cycloalkyl or aralkyl; and
each of Z and Z' is hydrogen, or taken together, a carbon-carbon bond.

The term "halo", as used herein, refers to bromo, chloro, fluoro or iodo. The term "lower alkyl", as used herein, refers to an alkyl group, straight or branched, having a chain length of one to six carbon atoms. The term "cycloalkyl", as used herein, refers to a cycloalkyl of three to eight carbon atoms. The term "aralkyl", as used herein, refers to aralkyl of seven to twelve carbon atoms, such as benzyl, phenethyl, methylbenzyl or naphthylmethyl. The term "lower alkoxy", as used herein, refers to lower alkoxy of one to six carbons, such as methoxy, ethoxy and propoxy.

The novel compounds of formula I are useful for the control of insects. The utility of these compounds as insect control agents is believed to be attributable to their juvenile hormone activity. They are preferably applied to the immature insect, namely — during the embryo, larvae or pupae stage in view of their ability to inhibit metamorphosis and otherwise cause abnormal development. These compounds are effective control agents for Hemipteran, such as Lygaeidae, Miridae and Pyrrhocoridae; Coleopteran, such as Tenebrionidae; Lepidopteran, such as Pyralidae, Noctiidae and Gelechiidae; Dipteran, such as mosquitoes; Orthoptera, such as roaches; and Homoptera, such as aphids. The compounds can be applied at low dosage levels of the order of 0.001 μg. to 25 μg. per insect. Suitable carrier substances include liquid or solid carriers, such as water, mineral or vegetable oils, talc, silica and natural or synthetic resin. The control of insects in accordance with the present invention is accomplished by spraying, dusting or exposing the insects to the vapor of the novel compounds. Generally, a concentration of less than 50% of the active compound is employed. The formulation can include insect attractants, emulsifying agents and wetting agents to assist in the application and efficiency of the active ingredient.

The compounds of formula I include lower alkyl and lower alkoxy substituted phenyl, i.e. wherein $Y_q$ is lower alkyl or lower alkoxy, which are exemplified by 4-ethylphenyl, 3-ethylphenyl, 2-ethylphenyl, 3,5-dimethylphenyl, 3,4-dimethylphenyl, 2,6-dimethylphenyl, 2,5-dimethylphenyl, 2,4-dimethylphenyl, 2,3-dimethylphenyl, 2,6-dimethylphenyl diisopropylphenyl, 3,5-di-t-butylphenyl, 2,6-di-sec-butylphenyl, 2,5-di-t-butylphenyl, 2,4-di-t-butylphenyl, 2,6-di-t-butyl-4-methylphenyl, 4-t-butylphenyl, 3-t-butylphenyl, 4-sec-butylphenyl, 2-t-butylphenyl, 2-sec-butylphenyl, 4-t-butyl-2-methylphenyl, 2-t-butyl-6-methylphenyl, 2-t-butyl-5-methylphenyl, 2-t-butyl-4-methylphenyl, 4-t-amylphenyl, 2-isopropylphenyl, 3-isopropylphenyl, 2-n-propylphenyl, 4-n-propylphenyl, 2,3,5,6-tetramethylphenyl, 2,4,6-tri-t-butylphenyl, 2,3,5-trimethylphenyl, 2,3,6-trimethylphenyl, 2,4,6-trimethylphenyl, 3,4,5-trimethylphenyl, 4-isopropylphenyl, 2-methyl-4,6-dinitrophenyl, 2-methyl-4-chlorophenyl, 2-chloro-4-t-butylphenyl, 2-chloro-4,5-dimethylphenyl, 2,6-dimethyl-4-nitrosophenyl, 2,6-dimethyl-4-nitrophenyl, 2,4-dichloro-6-methylphenyl, 2,4-dichloro-5-methylphenyl, 2,6-di-t-butyl-4-nitrosophenyl, 2,6-dibromo-4-methylphenyl, 4-chloro-2,3,6-trimethylphenyl, 4-chloro-3-methylphenyl, 4-chloro-2-methylphenyl, 2-chloro-6-methylphenyl, 4-chloro-3,5-dimethylphenyl, 4-chloro-2,6-dimethylphenyl, 4-chloro-2,5-dimethylphenyl, 2-chloro-4,5-dimethylphenyl, 4-t-butyl-2-chlorophenyl, 2-bromo-4-methylphenyl, 4-bromo-3,5-dimethylphenyl, 2-bromo-4,5-dimethylphenyl, 2-methyl-3-nitrophenyl, 3-methyl-4-nitrophenyl, 4-methyl-3-nitrophenyl, 5-methyl-2-nitrophenyl, 2-methyl-4-nitrosophenyl, 3-methyl-4-nitrosophenyl and 2-methoxy-4-methylphenyl and lower alkoxyphenyl, such as 3,5-dimethoxyphenyl, 2,6-dimethoxyphenyl, 2,3-dimethoxyphenyl, 4-n-butoxyphenyl, 4-methoxyphenyl, 4-ethoxyphenyl, 2-ethoxy-4-nitrophenyl, 2-methoxy-4-nitrophenyl, 2-methoxy-4-chlorophenyl and 3-methoxyphenyl.

Examples of other phenyl groups included in formula I are 4-nitrosophenyl, 2-chloro-4-nitrosophenyl, 2-chloromethyl-4-nitrophenyl, 3-trifluoromethyl-2,4,6-trinitrophenyl, 4-cyanophenyl, 3-cyanophenyl, 2-cyanophenyl, 4-methylthiophenyl, 4-trifluoromethylphenyl, 3-trifluoromethylphenyl, 2,5-dichloro-4-methoxyphenyl, 2,6-dichloro-4-(methylsulfonyl)phenyl, 3,5-dichloro-4-(methylsulfonyl)phenyl and 2,5-dichloro-4-methylthiophenyl.

In the description following, each of R to $R^{10}$, m, n, p, q, r, s, t and v is as defined above.

The compounds of formula I are conveniently prepared from the olefin precursors of formulas II, III or IV (W' is oxygen or sulfur):

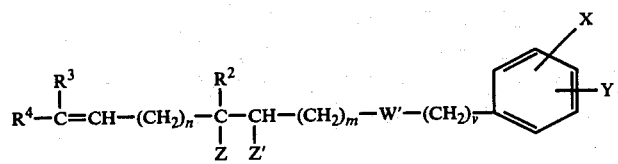
(II)

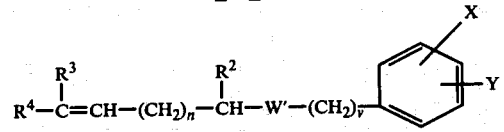
(III)

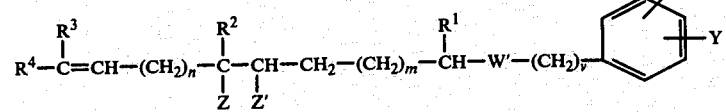
(IV)

-continued

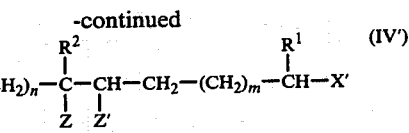
(IV')

using mercuric salt followed by reduction of the oxymercurial intermediate in situ. Thus, an olefin of II, III or IV is reacted with, for example, mercuric acetate in aqueous ether followed by reduction to yield the corresponding compound of formula IA, IB or IC wherein $R^5$ is —OR in which R is hydrogen. By conducting the reaction in the presence of an alcohol (R—OH), such as methanol, ethanol, isopropyl alcohol, benzyl alcohol, cyclopentanol, and the like, the corresponding ether ($R^5$ is —OR) is obtained. Suitable mercuric salts include mercuric acetate, mercuric nitrate, mercuric trifluoroacetate, mercuric acylates and mercuric halides. Suitable reducing agents include the borohydrides, hydrazine and sodium amalgam. See Brown and Rei, *J. Am. Chem. Soc.* 91, 5646 (1969); Brown et al., *J. Am. Chem. Soc.* 89, 1522 and 1524 (1967); and Wakabayashi, *J. Med. Chem.* 12, 191 (January 1969).

An alternative process for preparation of the compounds of the present invention is to first carry out the addition of water or alcohol, as described above, and then form the ether or thioether by alkylation of a salt of the appropriate phenol or phenyl mercaptan. That is, alkylation of the salt of the phenyl compound (XI):

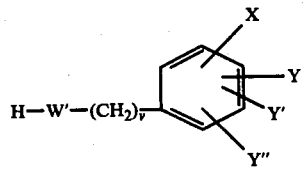

with the alkylating agent of formula II', III' or IV' (X' is bromo or chloro):

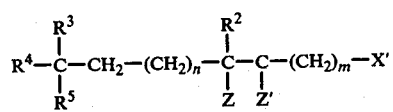
(II')

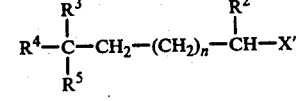
(III')

The foregoing method is preferred when Y" is a group containing SO or $SO_2$.

The sulfinyl compounds (W is SO) are prepared by treatment of a thioether with sodium metaperiodate, hydrogen peroxide, or the like, at a temperature of from about 0° to 20° C. for about one to six hours. The reaction usually affords some of the sulfonyl compound also which can be separated by chromatography. By using more than one mole of sodium periodate or hydrogen peroxide, higher temperature and longer reaction time, the reaction favors formation of the sulfonyl compounds. Preparation of sulfinyl and sulfonyl compounds is described by N. J. Leonard et al., *Journal of Organic Chemistry* 27, 282 (1962).

The bromide and chloride of formula II' can be prepared from the corresponding C-1 alcohol which is obtained by reduction of an acid or ester of the formula VII (m' is zero or one):

$$R^4-\overset{R^3}{\underset{}{C}}=CH-(CH_2)_n-\overset{R^2}{\underset{}{C}}=CH-(CH_2)_{m'}-COOR^6 \quad (VII)$$

in which $R^6$ is hydrogen or lower alkyl, using lithium aluminum hydride, or the like. The overall synthesis is outlined as follows:

$$R^4-\overset{R^3}{\underset{}{C}}=O \xrightarrow{\text{Wittig}} R^4-\overset{R^3}{\underset{}{C}}=CH-(CH_2)_n-\overset{R^2}{\underset{}{C}}=O$$

(V)                                  (VI)

(VII) 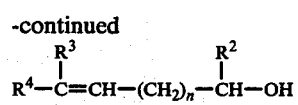

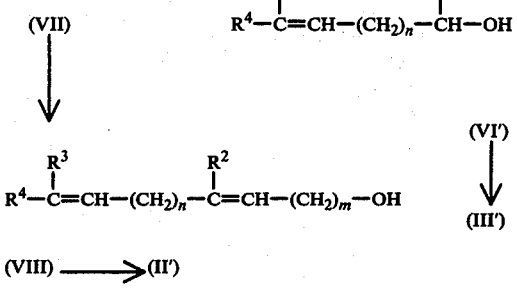

(VIII) ⟶ (II')

In the practice of the above process, a dialkyl ketone of formula V is reacted with a Wittig reagent of formula V' (φ is phenyl)

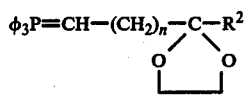 (V')

to form the ethylene ketal of a compound of formula VI which is hydrolyzed by treatment with acid to the ketone (VI). The ketone (VI) is then reacted with the carbanion of dialkyl carbalkoxyphosphonate to yield the $\alpha,\beta$-unsaturated ester (VII; m is zero and $R^6$ is lower alkyl) or with $\beta$-carboxyethyltriphenylphosphonium chloride in the presence of base to yield the $\beta,\gamma$-unsaturated acid (VII; m is one and $R^6$ is hydrogen). Suitable conditions are described in my application Ser. No. 7,987, filed Feb. 2, 1970 and by H. S. Corey et al., *J. Am. Chem. Soc.* 86, 1884–1885 (1964), the disclosures of which are incorporated by reference. The acid or ester (VII) is then reduced by conventional techniques using lithium aluminum hydride or like reducing agent to yield the primary alcohol (VIII) which is converted to the C-1 bromide or chloride (II') using phosphorus trichloride, phosphorus tribromide, phosphorus pentachloride, phosphorus pentabromide, and the like. Compounds of formula II' can be prepared also by using the synthesis of Bowers, *Science* 164, 323–325 (1969) which is incorporated by reference. The compounds of formula VI' are prepared by reduction of the ketone (VI) using sodium borohydride, lithium aluminum hydride, or the like, and the conversion of the secondary alcohol (VI') into the bromide or chloride (III') using phosphorus tribromide or phosphorus trichloride. The compounds of formula IV' are prepared by Wittig reaction of the ketone (VI) using the Wittig

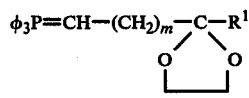

followed by hydrolysis with acid to yield the ketone

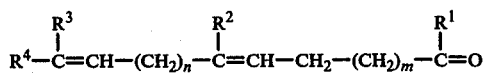

which is reduced using sodium borohydride, lithium aluminum hydride, or the like, to the alcohol which is treated with phosphorus trichloride, phosphorus tribromide, or the like, to yield the halide (IV'). Compounds of formula II' and IV' wherein each of Z and Z' is hydrogen are obtained by hydrogenation using paladium catalyst, or the like.

The starting compounds II, III and IV, in which W' is oxygen, can be prepared by the reaction of the appropriate phenol with an alkenyl bromide or chloride. The reaction is usually conducted by alkylation of a salt of the phenol with the bromide or chloride. See, for example, Bowers, *Science* 164, 323 (1969) and U.S. Pat. Nos. 3,764,517; 2,755,219; 2,832,792 and 2,920,993 in which there is described suitable methods.

The thio compounds of formulas II, III or IV (W' is sulfur) can be prepared by treating an alkenyl bromide or chloride with a phenyl mercaptan in the presence of sodium hydroxide, sodium alkoxide, and the like. Alternatively, treatment of alkenyl halide with hydrogen sulfide in alcohol in the presence of base, such as sodium hydroxide. The thus-obtained aliphatic thiol, on treatment with sodium hydroxide, potassium hydroxide, or the like, furnishes the corresponding alkali mercaptide which, on treatment with a phenyl bromide or chloride, furnishes the thioethers or sulfides of formulas II, III and IV (W' is sulfur).

The following examples are provided to illustrate the practice of the present invention and the preparation of the novel compounds. Temperature in degrees Centigrade.

EXAMPLE 1

(A) 3,7-Diethylnona-2,6-dien-1-ol (4.8 g.) is dissolved in 40 ml. of ether, cooled to −50° and 2.44 g. of phosphorus tribromide in 5 ml. of ether is added over 20 minutes. The reaction mixture is stirred for two hours, poured into ice and extracted with ether. The ethereal extracts are combined, washed with 10% sodium carbonate, water and saturated sodium chloride, dried over sodium sulfate and the solvent concentrated to yield 1-bromo-3,7-diethylnona-2,6-diene.

(B) To a suspension of 1 g. of sodium hydride (washed with pentane) in 10 ml. of tetrahydrofuran, under argon, and cooled to 4°, is added 3.38 g. of p-ethylphenol in 15 ml. of tetrahydrofuran over one hour. The reaction mixture is stirred for about 16 hours.

To the above-prepared sodium salt solution of p-ethylphenol, cooled in an ice-bath, is added with ether concentrate of the allylic bromide from Part A over 1.5 hours. After 1.75 hours, the reaction is warmed to room temperature and allowed to stand about 16 hours. The reaction is poured into water and extracted with ether. The ethereal extracts are combined, washed with 10% NaOH, water and saturated sodium chloride, dried over sodium sulfate and solvents evaporated to yield 1-(3',7'-diethylnona-2',6'-dienyloxy)-4-ethylbenzene.

(C) The procedure of Part A is repeated with the exception of using an equal amount of the C-1 alcohols listed in Column I to afford the corresponding C-1 bromide listed in Column II.

I 3,7-dimethylocta-2,6-dien-1-ol,
3-methyl-7-ethylnona-2,6-dien-1-ol,
3,7-dimethylnona-2,6-dien-1-ol,
4-methyl-8-ethyldeca-3,7-dien-1-ol,
4,8-dimethyldeca-3,7-dien-1-ol,
4,8-dimethylnona-3,7-dien-1-ol,
1,5-dimethylhex-4-en-1-ol,
3,7-dimethyloct-6-en-1-ol.

II 1-bromo-3,7-dimethylocta-2,6-diene,
1-bromo-3-methyl-7-ethylnona-2,6-diene,
1-bromo-3,7-dimethylnona-2,6-diene,
1-bromo-4-methyl-8-ethyldeca-3,7-diene,
1-bromo-4,8-dimethyldeca-3,7-diene,
1-bromo-1,5-dimethylhex-4-ene.
1-bromo-3,7-dimethyloct-6-ene.

The C-1 chlorides are prepared in the same way using phosphorus trichloride in place of phosphorus tribromide.

(D) By repeating the process of Part B using the bromides listed in Column II as the starting material, the corresponding p-ethylphenyl ethers listed in Column III are obtained.

III 1-(3',7'-dimethylocta-2',6'-dienyloxy)-4-ethylbenzene,
1-(3'-methyl-7'-ethylnona-2',6'-dienyloxy)-4-ethylbenzene,
1-(3',7'-dimethylnona-2',6'-dienyloxy)-4-ethylbenzene,
1-(4'-methyl-8'-ethyldeca-3',7'-dienyloxy)-4-ethylbenzene,
1-(4',8'-dimethyldeca-3',7'-dienyloxy)-4-ethylbenzene,
1-(4',8'-dimethylnona-3',7'-dienyloxy)-4-ethylbenzene,
1-(1',5'-dimethylhex-4'-enyloxy)-4-ethylbenzene,
1-(3',7'-dimethyloct-6'-enyloxy)-4-ethylbenzene.

EXAMPLE 2

(A) To a solution of 2 g. of 1-(3',7'-dimethylocta-2',6'-dienyloxy)-4-ethylbenzene in 20 ml. of ethanol, cooled to 0° by an ice bath, is added a suspension of 2.32 g. of mercuric acetate in 50 ml. of ethanol over 15 minutes. The reaction mixture is stirred for two hours and then, with cooling, 1.22 g. of potassium hydroxide in 20 ml. of ethanol is added. Then 0.139 g. of sodium borohydride is added in small portions and stirring continued 30 minutes. The solution is decanted, then concentrated to half volume, diluted with 100 ml. of water and extracted with ether (3 × 50). The ethereal phase is washed with water, dried over magnesium sulfate, and the crude product chromatographed on silica using hexane:ether to yield 1-(3',7'-dimethyl-7'-ethoxyoct-2'-enyloxy)-4-ethylbenzene.

(B) The foregoing process of Part A is repeated with the exception of replacing 1-(3',7'-dimethylocta-2',6'-dienyloxy)-3,4-methylenedioxybenzene with an equal amount of each of:
1-(3',7'-diethylnona-2',6'-dienyloxy)-4-ethylbenzene,
1-(3'-methyl-7'-ethylnona-2',6'-dienyloxy)-4-ethylbenzene,
1-(3',7'-dimethylnona-2',6'-dienyloxy)-4-ethylbenzene,
1-(4'-methyl-8'-ethyldeca-3',7'-dienyloxy)-4-ethylbenzene,
1-(4',8'-dimethyldeca-3',7'-dienyloxy)-4-ethylbenzene,
1-(4',8'-dimethylnona-3',7'-dienyloxy)-4-ethylbenzene,
1-(1',5'-dimethylhex-4'-enyloxy)-4-ethylbenzene,
1-(3',7'-dimethyloct-6'-enyloxy)-4-ethylbenzene to yield
1-(3',7'-diethyl-7'-ethoxynon-2'-enyloxy)-4-ethylbenzene,
1-(3'-methyl-7'-ethyl-7'-ethoxynon-2'-enyloxy)-4-ethylbenzene,
1-(3',7'-dimethyl-7'-ethoxynon-2'-enyloxy)-4-ethylbenzene,
1-(4'-methyl-8'-ethyl-8'-ethoxydec-3'-enyloxy)-4-ethylbenzene,
1-(4',8'-dimethyl-8'-ethoxydec-3'-enyloxy)-4-ethylbenzene,
1-(4',8'-dimethyl-8'-ethoxynon-3'-enyloxy)-4-ethylbenzene,
1-(1',5'-dimethyl-5'-ethoxyhexanyloxy)-4-ethylbenzene
1-(3',7'-dimethyl-7'-ethoxyoctanyloxy)-4-ethylbenzene.

By use of each of methanol, n-propanol, i-propanol or n-butanol in the foregoing process of this example in place of ethanol, the corresponding alcohol additives are obtained. For example, the use of an equal amount of methanol, n-propanol, i-propanol or n-butanol in place of ethanol in Part A yields each of 1-(3',7'-dimethyl-7'-methoxyoct-2'-enyloxy)-4-ethylbenzene, 1-[3',7'-dimethyl-7'-(n-propoxy)oct-2'-enyloxy]-4-ethylbenzene, 1-[3',7'-dimethyl-7'-(i-propoxy)oct-2'-enyloxy]-4-ethylbenzene and 1-[3',7'-dimethyl-7'-(n-butoxy)oct-2'-enyloxy]-4-ethylbenzene, respectively.

EXAMPLE 3

To a mixture of 1.9 g. of mercuric acetate, 6 ml. of water and 20 ml. of tetrahydrofuran is added 1.4 g. of 1-(3',7'-diethylnona-2',6'-dienyloxy)-4-ethylbenzene slowly. After addition is complete, the reaction mixture is stirred for about 20 minutes. The mixture is cooled to about 0° and 6 ml. of aqueous sodium hydroxide (3 molar) is added followed by 0.49 g. of sodium borohydride in aqueous sodium hydroxide (about 3 molar). The mixture is stirred for about 30 minutes. The mixture is then decanted, concentrated, diluted with water and then extracted with ether. The ethereal extract is washed with water, dried over magnesium sulfate and the product chromatographed on silica to yield 1-(7'-hydroxy-3',7'-diethylnon-2'-enyloxy)-4-ethylbenzene.

The above process is repeated with the exception of using the ethers listed in Column III as the starting material to yield the corresponding hydroxy substituted ether, that is:
1-(7'-hydroxy-3',7'-dimethyloct-2'-enyloxy)-4-ethylbenzene,
1-(7'-hydroxy-3'-methyl-7'-ethylnon-2'-enyloxy)-4-ethylbenzene,
1-(7'-hydroxy-3',7'-dimethylnon-2'-enyloxy)-4-ethylbenzene,
1-(8'-hydroxy-4'-methyl-8'-ethyldec-3'-enyloxy)-4-ethylbenzene,
1-(8'-hydroxy-4',8'-dimethyldec-3'-enyloxy)-4-ethylbenzene,
1-(8'-hydroxy-4',8'-dimethylnon-3'-enyloxy)-4-ethylbenzene,
1-(5'-hydroxy-1',5'-dimethylhexanyloxy)-4-ethylbenzene,
1-(7'-hydroxy-3',7'-dimethyloctanyloxy)-4-ethylbenzene.

EXAMPLE 4

To a solution of 2 g. of sodium in 50 ml. of methanol at about 0° is added 35 g. of p-ethylphenylmercaptan. After about 0.5 hour, 15 g. of 1-bromo-3,7-dimethylocta-2,6-diene is added and then the mixture is refluxed for about two hours. Then the solvent is evaporated and the concentrate taken up in petroleum ether which is washed with water, dried over magnesium sulfate and evaporated under reduced pressure to yield 1-(p-ethylphenyl)thio-3,7-dimethylocta-2,6-diene which can be purified by chromatography.

By using the other bromides listed in Column II as the starting material, the corresponding thioethers are prepared.

An alternative process for the preparation of the thioethers is to prepare the thiol of the C-1 bromides listed in Column II as follows:

To a solution of 2 g. of sodium hydroxide in 40 ml. of methanol saturated with hydrogen sulfide is added 14 g. of 1-bromo-3,7-dimethylocta-2,6-diene. The mixture is stirred at about 25° for about five hours with continued introduction of hydrogen sulfide. The mixture is diluted with water and then extracted with petroleum ether. The organic phase is washed well with water, dried over sodium sulfate and evaporated under reduced pressure to yield 3,7-dimethylocta-2,6-dienylmercaptan which is purified by chromatography.

The thus-obtained thiol is then reacted with 1-bromo-4-ethylbenzene in the presence of base as above to yield the thioether.

EXAMPLE 5

To a solution of 2 g. of 1-(4'-ethylphenyl)thio-3,7-dimethylocta-2,6-diene in 20 ml. of ethanol, cooled to 0°, is added a suspension of 2.3 g. of mercuric acetate in 50 ml. of ethanol over 15 minutes. The reaction mixture is stirred for two hours and then, with cooling, 1.2 g. of potassium hydroxide in 20 ml. of ethanol is added. Then 0.14 g. of sodium borohydride is added in small portions and stirring continued for about 30 minutes. The solution is then decanted, concentrated to half volume, diluted with 100 ml. of water and extracted with ether. The ethereal phase is washed with water, dried over magnesium sulfate and evaporated under reduced pressure to yield 1-(4'-ethylphenyl)thio-7-ethoxy-3,7-dimethyloct-2-ene which is purified by chromatography.

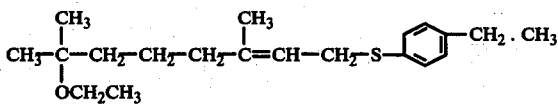

The foregoing process is used for the addition of alcohol to the other thioethers prepared as described in Example 4 to obtain the corresponding alkoxy thioethers. Similarly, the addition of water to the thioethers is accomplished using the process of Example 3 to prepare the hydroxy substituted thioethers of the present invention.

EXAMPLE 6

To 210 ml. of a 0.5M solution of sodium metaperiodate (aqueous methanol 1:1) at 0° is added 0.1 mole of 1-(4'-ethylphenyl)thio-7-ethoxy-3,7-dimethyloct-2-ene. The mixture is stirred at 0° for four hours and then filtered to remove precipitated sodium iodate. The filtrate is diluted with water and then extracted with chloroform. The extract is dried over magnesium sulfate and solvent removed by evaporation under reduced pressure to yield p-ethylphenyl 7-ethoxy-3,7-dimethyloct-2-enylsulfoxide.

Other sulfoxides (W is SO) of the present invention are prepared using the foregoing process.

EXAMPLE 7

To 200 ml. of aqueous methanol (1:1) containing 0.2 moles of sodium metaperiodate is added 0.1 mole of 1-(4'-ethylphenyl)thio-7-ethoxy-3,7-dimethyloct-2-ene. The mixture is maintained at about 30° for six hours. After cooling, the mixture is filtered to remove precipitated sodium iodate. The filtrate is diluted with water and then extracted with chloroform. The extract is dried over magnesium sulfate and solvent removed by evaporation to yield p-ethylphenyl 7-ethoxy-3,7-dimethyloct-2-enylsulfone which can be purified by chromatography on silica.

Using the above process, the other sulfones (W is $SO_2$) of the present invention are prepared.

EXAMPLE 8

(A) To a solution of 20.9 g. of the ethylene ketal of 1-bromo-4-pentanone (obtained by treating 1-bromo-4-pentanone with ethylene glycol in benzene in the presence of p-toluenesulfonic acid) in 100 ml. of benzene is added 20 g. of triphenylphosphine. The mixture is heated at reflux temperature for two hours and then filtered. The solid material thus-collected is washed with benzene, dried in vacuo and added to 6.49 g. of butyl lithium in 50 ml. of dimethylsulfoxide. The mixture is stirred until an orange solution is obtained and 38 g. of methyl ethyl ketone is then added. The mixture is stirred at about 25° for about eight hours, poured into water and then extracted with ether. The ethereal phase is concentrated and the concentrate added to 0.1N solution of hydrochloric acid in aqueous acetone and stirred for about 15 hours. The mixture is then poured into ice water and extracted with ethyl acetate. The extracts are combined, washed with water, dried over sodium sulfate and evaporated to yield 6-methyl-5-octen-2-one which is purified by chromatography and separated into the cis and trans isomer.

By repeating the above process using the ethylene ketal of each of 1-bromo-5-hexanone and 1-bromo-4-hexanone, there is obtained 7-methyl-6-nonen-2-one and 7-methyl-6-nonen-3-one.

(B) A mixture of 11.2 g. of diethyl carbomethoxymethylphosphonate in 100 ml. of dimethylformamide is treated with 2.4 g. of sodium hydride. The mixture is stirred until the evolution of gas ceases and then 10 g. of 7-methyl-6-nonen-2-one is added slowly with stirring, maintaining temperature below 30°. The mixture is stirred for about one hour, then diluted with water and then extracted with ether. The ethereal phase is washed with water, dried over sodium sulfate and evaporated under reduced pressure to yield methyl 3,8-dimethyldeca-2,7-dienoate as a mixture of isomers (trans,cis; trans,trans; cis,cis and cis,trans) which are separated by chromatography.

(C) Six grams of 6-methyl-5-octen-2-one is added to a solution of 3.0 g. of sodium borohydride, 80 ml. of methanol and 6 ml. of 2N sodium hydroxide solution. After about two hours, acetic acid is added to destroy excess sodium borohydride and the solution poured into water and extracted with ether. The combined ether extracts are washed with aqueous sodium bicarbonate, water and brine, dried and evaporated to yield 6-methyl-5-octen-2-ol which is purified by chromatography.

Similarly, 7-methyl-6-nonen-2-one and 7-methyl-6-nonen-3-one is reduced to 7-methyl-6-nonen-2-ol and 7-methyl-6-nonen-3-ol.

Triphenylphosphite benzoylchloride (10 g.) is mixed with 1.9 g. of 6-methyl-5-octen-2-ol and kept at room temperature overnight. The crude product is washed with 2N sodium hydroxide and water and dried to yield 2-chloro-6-methyl-5-octene.

Alternatively, the method of Example 1 is used to prepare the bromide and chloride.

(D) A solution of 2 g. of methyl 3,8-dimethyldeca-2,7-dienoate in 20 ml. of dry ether is added with stirring to 0.4 g. of lithium aluminum hydride covered in ether at 0°. After about one hour, 2.5 ml. of acetic acid is added. The mixture is washed with ice water and the ether phase dried and evaporated to yield 3,8-dimethyldeca-2,7-dien-1-ol which is treated with phosphorus tribromide to yield 1-bromo-3,8-dimethyldeca-2,7-diene.

(E) 6-Methyl-5-hepten-2-one is converted into 4,8-dimethylnona-3,7-dienoic acid by reaction with β-carboxyethyltriphenylphosphonium chloride in dimethylsulfoxide using the method of H. S. Corey et al., *J. Am. Chem. Soc.* 86, 1884 (1964). The trans and cis isomer can be separated by chromatography at this point or a mixture of the two isomers employed in further reactions. The acid is then converted into the acid chloride using thionyl chloride at roomm temperature or slightly higher. The acid chloride is then treated with an alcohol, such as methanol or ethanol, at a temperature of about 40° for a few minutes to yield the ester, methyl 4,8-dimethylnona-3,7-dienoate and ethyl 4,8-dimethylnona-3,7-dienoate.

By use of the above procedure, each of 7-methyl-6-nonen-2-one and 6-methyl-5-octen-2-one is converted into methyl 4,9-dimethylundeca-3,8-dienoate and methyl 4,8-dimethyldeca-3,7-dienoate, respectively.

Following the procedure of Part D above, each of the esters is reduced to the C-1 alcohol, i.e. 4,8-dimethylnona-3,7-dien-1-ol, 4,9-dimethylundeca-3,8-dien-1-ol and 4,8-dimethyldeca-3,7-dien-1-ol and then to the C-1 bromide, namely, 1-bromo-4,8-dimethylnona-3,7-diene, 1-bromo-4,9-dimethylundeca-3,8-diene and 1-bromo-4,8-dimethyldeca-3,7-diene, respectively.

EXAMPLE 9

To a solution of 1.7 g. of methyl 4,8-dimethylnona-3,7-dienoate in 20 ml. of ethanol, cooled to about 0°, is added a suspension of 2.3 g. of mercuric acetate in 50 ml. of ethanol, over about 15 minutes. The reaction mixture is stirred for two hours and then, with cooling, 1.2 g. of potassium hydroxide in 20 ml. of ethanol is added. Then 0.26 g. of sodium borohydride is added in small portions and stirring continued 30 minutes. The solution is decanted, concentrated to half volume, diluted with water and extracted with ether. The ethereal phase is washed with water, dried over magnesium sulfate and the product chromatographed to yield methyl 8-ethoxy-4,8-dimethylnon-3-enoate.

The methyl ester, methyl 8-ethoxy-4,8-dimethylnon-3-enoate is reduced using lithium aluminum hydride following the procedure of Example 8, Part D, to the alcohol, 8-ethoxy-4,8-dimethylnon-3-en-1-ol.

Using the foregoing procedure, each of methyl 4,9-dimethylundeca-3,8-dienoate and methyl 4,8-dimethylundeca-3,7-dienoate is converted into 9-ethoxy-4,9-dimethylundec-3-en-1-ol and 8-ethoxy-4,8-dimethyldec-3-en-1ol. Following the procedure of, for example, Example 1 (A and then B), the C-1 alcohols thus-obtained are converted into the C-1 bromide and then the p-ethylphenyl ether.

A suspension of 0.5 g. of 5% palladium-on-carbon catalyst in 50 ml. of benzene is hydrogenated for 30 minutes. A mixture of 1.5 g. of 9-ethoxy-4,9-dimethylundec-3-en-1-ol in 75 ml. of methanol is added and hydrogenated with agitation until the theoretical amount of hydrogen is absorbed. The catalyst is removed by filtration and the solution evaporated to yield 9-ethoxy-4,9-dimethylundecan-1-ol which is purified by chromatography. The product is treated with phosphorus tribromide to yield 1-bromo-9-ethoxy-4,9-dimethylundecane which can be used as the alkylating agent for preparation of compounds of the present invention of formula I.

The foregoing hydrogenation procedure can be used for preparing the saturated derivatives of the present invention (i.e. when each of Z and Z' is hydrogen) by hydrogenation of the final product or intermediates therefor.

EXAMPLE 10

(A) 100 Grams of 3,7-dimethyloct-6-en-1-ol is dissolved in 150 ml. of pyridine and 100 ml. of acetic anhydride and left at room temperature for about 48 hours. Then the mixture is extracted with ether and the ethereal extracts washed with water, 10% aqueous HCl and brine to yield 1-acetoxy-3,7-dimethyloct-6-ene which is purified by distillation.

(B) 150 Grams of mercuric acetate in 400 ml. of dry ethanol is added to 100 g. of 1-acetoxy-3,7-dimethyloct-6-ene (citronellol acetate) in 200 ml. of dry ethanol cooled in an ice bath. The temperature is allowed to come to room temperature by standing overnight. Then the mixture is cooled to 0°, 100 g. of potassium hydroxide in 1.5 l. of ethanol is added followed by addition of 10 g. of sodium borohydride in small portions. After about 30 minutes at 0°, water (100 ml.) is added and mixture left at room temperature for two hours. The mixture is filtered, filtrate concentrated and extracted with ether. The ethereal extract is washed, dried and evaporated to yield 7-ethoxy-3,7-dimethyloctan-1-ol which is purified by distillation or chromatography.

By using methanol in the foregoing process in place of ethanol, there is obtained 7-methoxy-3,7-dimethyloctan-1-ol.

(C) To 10 g. of 7-ethoxy-3,7-dimethyloctan-1-ol in 250 ml. of methylene chloride and 10 ml. of triethylamine at −5° to 0° is added slowly 6.5 ml. of mesyl chloride. About 15 minutes after addition is complete, the reaction is worked up by pouring onto ice, added more methylene dichloride, extracted with ice water, washed with 10% HCl, saturated sodium bicarbonate, brine and dried to yield the mesylate (XX) which can be purified by chromatography. Cf. Crossland et al., *J. Org. Chem.* 35, No. 9, 3195 (1970).

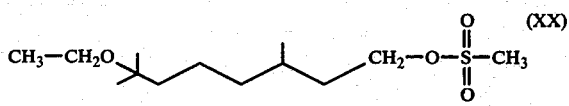

(D) A mixture of 1.4 g. of p-ethylphenol and 2.8 g. of potassium carbonate in 50 ml. of dimethylformamide is stirred at 100° under nitrogen for about 15 minutes. Three g. of the mesylate of Part C is added and the mixture heated at 100° for about three hours. The reaction is allowed to cool and then worked up by extraction with ether and washing with dilute sodium hydroxide and brine to yield 7-ethoxy-3,7-dimethyloctyl p- ethylphenyl ether [1-(7'-ethoxy-3',7'-dimethyloctanyloxy)-4-ethylbenzene] which can be purified by chromatography eluting with ethyl acetate:hexane.

EXAMPLE 11

Following the procedure of Example 10(A), other alcohols of VIII and alcohols of formula VI' are converted to the corresponding acetate and then addition of alcohol using the procedure of Example 10(B) followed by conversion to the corresponding methanesulfonate of formulas XXI and XXII or the halides XXIII and XXIV using the procedure of Example 1(A) and (C) wherein $R^{12}$ is alkyl, cycloalkyl or aralkyl and X' is bromo or chloro.

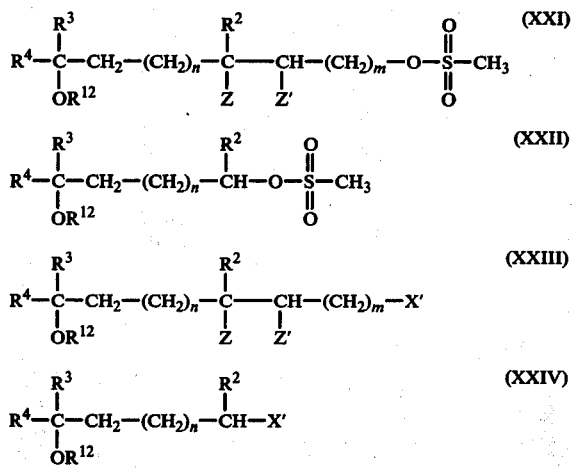

(A) The addition of ethanol to the acetate of each of 6-methyloct-5-en-2-ol, 6-methylhept-5-en-2-ol, 4,8-dimethylnona-3,7-dien-1-ol, 3,7-dimethylnona-2,6-dien-1-ol, 3,8-dimethyldeca-2,7-dien-1-ol and 3,7-dimethylocta-2,6-dien-1-ol following the procedure of Example 10(B) yields 6-ethoxy-6-methyloctan-2-ol, 6-ethoxy-6-methylheptan-2-ol, 8-ethoxy-4,8-dimethylnon-3-en-1-ol, 7-ethoxy-3,7-dimethylnon-2-en-1-ol, 8-ethoxy-3,8-dimethyldec-2-en-1-ol and 7-ethoxy-3,7-dimethyloct-2-en-1-ol, respectively.

The addition of methanol is accomplished by the same procedure to yield each of 6-methoxy-6-methyloctan-2-ol, 6-methoxy-6-methylheptan-2-ol, 8-methoxy-4,8-dimethylnon-3-en-1-ol, 7-methoxy-3,7-dimethylnon-2-en-1-ol, 8-methoxy-3,8-dimethyldec-2-en-1-ol and 7-methoxy-3,7-dimethyloct-2-en-1-ol, respectively.

Using the same procedure, each of n-propanol, isopropyl alcohol, n-butanol, n-pentanol, n-hexanol and benzyl alcohol is added to the terminal double to yield the corresponding n-propoxy, isopropoxy, n-butoxy, n-pentoxy, n-hexoxy and benzyloxy derivatives.

(B) Following the procedure of Example 10(C), the alcohols of Part A are converted to the mesylates of formulas XXI and XXII.

(C) Following the procedure of Example 1, the alcohols of Part A are converted to the corresponding bromide, i.e. 2-bromo-6-ethoxy-6-methyloctane, 2-bromo-6-ethoxy-6-methylheptane, 1-bromo-8-ethoxy-4,8-dimethylnon-3-ene, 1-bromo-7-ethoxy-3,7-dimethylnon-2-ene, 1-bromo-8-ethoxy-3,8-dimethyldec-2-ene and 1-bromo-7-ethoxy-3,7-dimethyloct-2-ene and the corresponding methoxy derivatives.

Similarly, using phosphorous trichloride or triphenylphosphite benzoyl chloride, the corresponding chlorides are obtained.

EXAMPLE 12

(A) The mesylate of each of 7-methoxy-3,7-dimethyloctan-1-ol, 7-methoxy-3,7-dimethyloct-2-en-1-ol and 6-methoxy-6-methylheptan-2-ol is reacted with p-ethylphenol using the process of Example 10(D) to yield 7-methoxy-3,7-dimethyloctyl p-ethylphenyl ether, 7-methoxy-3,7-dimethyloct-2-enyl p-ethylphenyl ether and 6-methoxy-6-methylhept-2-yl p-phenyl ether (5-methoxy-1,5-dimethylhexyl p-ethylphenyl ether).

(B) The process of Example 10(D) is repeated using each of 3-ethylphenol, 4-t-butylphenol, 4-isopropylphenol, 2-methyl-4-chlorophenol, 2,4-dichloro-6-methylphenol, 2-bromo-4-methylphenol, 4-trifluoromethylphenol, 4-ethoxyphenol, 2-methoxy-4-chlorophenol, 4-nitrosophenol, 3-trifluoromethylphenol, 2,5-dichloro-4-methoxyphenol, 4-methylthiophenol and 2,5-dichloro-4-methylthiophenol in place of p-ethylphenol to yield each of 1-(7'-ethoxy-3',7'-dimethyloctyloxy)-3-ethylbenzene, 1-(7'-ethoxy-3',7'-dimethyloctyloxy)-4-t-butylbenzene, 1-(7'-ethoxy-3',7'-dimethyloctyloxy)-4-isopropylbenzene, 1-(7'-ethoxy-3',7'-dimethyloctyloxy)-2-methyl-4-chlorobenzene, 1-(7'-ethoxy-3',7'-dimethyloctyloxy)-2,4-dichloro-6-methylbenzene, 1-(7'-ethoxy-3',7'-dimethyloctyloxy)-2-bromo-4-methylbenzene, 1-(7'-ethoxy-3',7'-dimethyloctyloxy)-4-trifluoromethylbenzene, 1-(7'-ethoxy-3',7'-dimethyloctyloxy)-4-ethoxybenzene, 1-(7'-ethoxy-3',7'-dimethyloctyloxy)-2-methoxy-4-chlorobenzene, 1-(7'-ethoxy-3',7'-dimethyloctyloxy)-4-nitrosobenzene, 1-(7'-ethoxy-3',7'-dimethyloctyloxy)-3-trifluoromethylbenzene, 1-(7'-ethoxy-3',7'-dimethyloctyloxy)-2,5-dichloro-4-methoxybenzene, 1-(7'-ethoxy-3',7'-dimethyloctyloxy)-4-methylthiobenzene and 1-(7'-ethoxy-3',7'-dimethyloctyloxy)-2,5-dichloro-4-methylthiobenzene, respectively.

By using the mesylate of 7-methoxy-3,7-dimethyloctan-1-ol in the foregoing procedure, the corresponding 7-methoxy-3,7-dimethyloctyl substituted phenyl ethers are obtained.

EXAMPLE 13

To 3.5 g. of sodium in 150 ml. of ethanol is added 18.8 g. of p-ethylphenyl mercaptan. The mixture is stirred for about 40 minutes and then 30 g. of 2-bromo-6-methoxy-6-methylheptane is added. The reaction mixture is heated under reflux for about 35 minutes, allowed to cool and then diluted with water. The reaction is worked up by extraction with ether, washing with water and drying over magnesium sulfate to yield 5-methoxy-1,5-dimethylhexyl p-ethylphenyl sulfide which can be purified by chromatography.

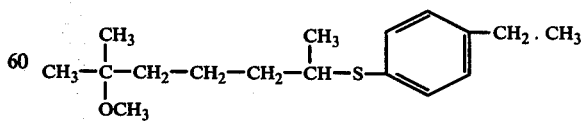

EXAMPLE 14

Following the procedure of Example 6, the sulfide of Example 13 is converted into p-ethylphenyl 5-methoxy-1,5-dimethylhexyl sulfoxide.

Using the procedure of Example 7, the sulfide of Example 13 is converted into p-ethylphenyl 5-methoxy-1,5-dimethyldimethylhexyl sulfone.

EXAMPLE 15

By using the process of either Example 4 or 13, each of 1-bromo-7-methoxy-3,7-dimethyloctane, 1-bromo-7-ethoxy-3,7-dimethyloctane, 1-bromo-7-methoxy-3,7-dimethyloct-2-ene and 1-bromo-7-ethoxy-3,7-dimethyloct-2-ene is reacted with p-ethylphenyl mercaptan to yield 7-methoxy-3,7-dimethyloctyl p-ethylphenyl sulfide, 7-ethoxy-3,7-dimethyloctyl p-ethylphenyl sulfide, 7-methoxy-3,7-dimethyloct-2-enyl p-ethylphenyl sulfide and 7-ethoxy-3,7-dimethyloct-2-enyl p-ethylphenyl sulfide, respectively. By use of the processes of Examples 6 and 7, the corresponding sulfoxides and sulfones, respectively, are prepared, e.g. 7-methoxy-3,7-dimethyloctyl p-ethylphenyl sulfoxide, 7-ethoxy-3,7-dimethyloctyl p-ethylphenyl sulfoxide, 7-methoxy-3,7-dimethyloctyl p-ethylphenyl sulfone and 7-ethoxy-3,7-dimethyloctyl p-ethylphenyl sulfone and the corresponding 2,3-dehydro compounds.

EXAMPLE 16

By use of the process of Example 1(B) or 10(D), each of the bromides under Column IV is used as the alkylating agent with 2-(3'-methylthiopropyl)-3,5-dimethylphenol to yield the corresponding ether, that is - 1-(7'-methoxy-3',7'-dimethyloctyloxy)-2-(3'-methylthiopropyl)-3,5-dimethylbenzene, 1-(7'-ethoxy-3',7'-dimethyloctyloxy)-2-(3'-methylthiopropyl)-3,5-dimethylbenzene, 1-(7'-methoxy-3',7'-dimethyloct-2'-enyloxy)-2-(3'-methylthiopropyl)-3,5-dimethylbenzene, 1-(7'-ethoxy-3',7'-dimethyloct-2'-enyloxy)-2-(3'-methylthiopropyl)-3,5-dimethylbenzene, 1-(1',5'-dimethyl-5'-methoxyhexyloxy)-2-(3'-methylthiopropyl)-3,5-dimethylbenzene and 1-(10'-methoxy-6',10'-dimethylundec-2'-yloxy)-2-(3'-methylthiopropyl)-3,5-dimethylbenzene, respectively.

IV 1-bromo-7-methoxy-3,7-dimethyloctane,
1-bromo-7-ethoxy-3,7-dimethyloctane,
1-bromo-7-methoxy-3,7-dimethyloct-2-ene,
1-bromo-7-ethoxy-3,7-dimethyloct-2-ene,
2-bromo-6-methoxy-6-methylheptane,
2-bromo-10-methoxy-6,10-dimethylundecane.

The thiophenol, 2-(3'-methylthiopropyl)-3,5-dimethylphenol, is prepared as described in U.S. Pat. No. 3,443,012. The other thiophenols of U.S. Pat. No. 3,443,012, which is incorporated by reference, serve as starting materials as described in this example to prepare the corresponding ethers.

EXAMPLE 17

By use of the process of either Example 1(B) or 10(D), 1-bromo-7-methoxy-3,7-dimethyloctane is reacted with 4-(methylsulfonyl)phenol to yield 1-(7'-methoxy-3',7'-dimethyloctyloxy)-4-(methylsulfonyl)benzene.

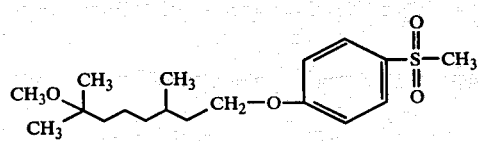

Similarly, the other bromides of Column IV are reacted with 4-(methylsulfonyl)phenol to yield 1-(7'-ethoxy-3',7'-dimethyloctyloxy)-4-(methylsulfonyl)benzene, 1-(7'-methoxy-3',7'-dimethyloct-2'-enyloxy)-4-(methylsulfonyl)benzene, 1-(7'-ethoxy-3',7'-dimethyloct-2'-enyloxy)-4-(methylsulfonyl)benzene, 1-(5'-methoxy-1',5'-dimethylhexyloxy)-4-(methylsulfonyl)benzene and 1-(10'-methoxy-6',10'-dimethylundeca-2'-yloxy)-4-(methylsulfonyl)benzene, respectively.

EXAMPLE 18

Each of the bromides of Column II is reacted with mercuric acetate in ethanol followed by sodium borohydride reduction using the procedure of Example 10(B) to yield 1-bromo-7-ethoxy-3,7-dimethyloct-2-ene, 1-bromo-7-ethoxy-7-ethyl-3-methylnon-2-ene, 1-bromo-7-ethoxy-3,7-dimethylnon-2-ene, 1-bromo-8-ethoxy-4-methyl-8-ethyldec-3-ene, 1-bromo-8-ethoxy-4,8-dimethyl-dec-3-ene, 1-bromo-5-ethoxy-1,5-dimethylhexane and 1-bromo-7-ethoxy-3,7-dimethyloctane.

EXAMPLE 19

Each of 2-methoxy-4-nitrophenol, 2-methyl-4,6-dinitrophenol, 2,4-dimethylthiophenol, 4-ethylthiophenol, 2-ethylphenol, 4-methylthio-3-ethylphenol, 2-methyl-4-ethylphenol, 2,4-diethylphenol, 2,6-diethylphenol and 2,6-dimethylphenol is alkylated using 1-bromo-7-ethoxy-3,7-dimethyloctane and the 2,3-dehydro thereof by the process of Example 1(B) or 10(D) to yield 7-ethoxy-3,7-dimethyloctyl 2-methoxy-4-nitrophenyl ether and the 2,3-dehydro; 7-ethoxy-3,7-dimethyloctyl 2-methoxy-4-nitrophenyl ether and the 2,3-dehydro; 7-ethoxy-3,7-dimethyloctyl 2-methyl-4,6-dinitrophenyl ether and the 2,3-dehydro; 7-ethoxy-3,7-dimethyloctyl 2,4-dimethylthiophenyl ether and the 2,3-dehydro; 7-ethoxy-3,7-dimethyloctyl 4-ethylthiophenyl ether and the 2,3-dehydro; 7-ethoxy-3,7-dimethyloctyl 2-ethylphenyl ether and the 2,3-dehydro; 7-ethoxy-3,7-dimethyloctyl 2-methyl-4-ethylphenyl ether and the 2,3-dehydro; 7-ethoxy-3,7-dimethyloctyl 2,4-diethylphenyl ether and the 2,3-dehydro; 7-ethoxy-3,7-dimethyloctyl 2,6-diethylphenyl ether and the 2,3-dehydro and 7-ethoxy-3,7-dimethyloctyl 2,6-dimethylphenyl ether and the 2,3-dehydro.

EXAMPLE 20

Each of 7-ethoxy-3,7-dimethyloctyl 2-chloro-4-t-butylphenyl ether, 7-ethoxy-3,7-dimethyloctyl 2-chloro-4,5-dimethylphenyl ether, 7-ethoxy-3,7-dimethyloctyl 4-methylthio-3,5-dimethylphenyl ether, 7-ethoxy-3,7-dimethyloctyl 2,6-diisopropylphenyl ether, 7-ethoxy-3,7-dimethyloctyl 2-isopropylphenyl ether and 7-ethoxy-3,7-dimethyloctyl 2-methyl-6-ethylphenyl ether is prepared by the alkylation of 2-chloro-4-t-butylphenol, 2-chloro-4,5-dimethylphenol, 4-methylthio-3,5-dimethylphenol, 2,6-diisopropylphenol, 2-isopropylphenol and 2-methyl-6-ethylphenol using 1-bromo-7-ethoxy-3,7-dimethyloctane or the mesylate of 7-ethoxy-3,7-dimethyloctan-1-ol as the alkylating agent. Similarly, using 1-bromo-7-ethoxy-3,7-dimethyloct-2-ene or the mesylate of 7-ethoxy-3,7-dimethyloct-2-en-1-ol as the alkylating agent, the corresponding 2,3-dehydro phenyl ethers are prepared.

EXAMPLE 21

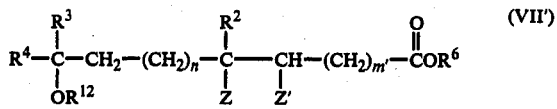

wherein, m' is zero or one; n is two or three; each of $R^2$, $R^3$ and $R^4$ is lower alkyl; $R^6$ is hydrogen or lower alkyl; $R^{12}$ is lower alkyl, cycloalkyl or aralkyl; and each of Z and Z' is hydrogen or, taken together, a carbon-carbon bond.

Compounds of the formula VII' are prepared using the process of Examples 8 and 9. Compounds of formula VII' wherein each of Z and Z' is hydrogen are prepared by hydrogenation using the process of Example 9.

To each of methyl 3,8-dimethyldeca-2,7-dienoate, methyl 4,8-dimethylnona-3,7-dienoate, methyl 3,7-dimethylocta-2,6-dienoate, methyl 3,7-dimethylnona-2,6-dienoate and methyl 4,9-dimethylundeca-3,8-dienoate is added methanol using the process of Example 9 to yield methyl 8-methoxy-3,8-dimethyldec-2-enoate, methyl 8-methoxy-4,8-dimethylnon-3-enoate, methyl 7-methoxy-3,7-dimethyloct-2-enoate, methyl 7-methoxy-3,7-dimethylnon-2-enoate and methyl 9-methoxy-4,9-dimethylundec-3-enoate, respectively.

EXAMPLE 22

Each of 2-ethylthiomethylphenol, 4-methylthiomethylphenol, 4-ethylthiomethylphenol, 2-t-butyl-4-methylthiomethylphenol, 2-t-butylthiomethyl-4-ethoxyphenol, 2-t-butylthiomethyl-4-methoxyphenol, 2-allyl-4-chlorophenol, 2-allyl-6-methoxyphenol, 2-allyl-4,6-dinitrophenol, 2-allyl-3,5-dichlorophenol, 4-cyanophenol, 4-n-butoxyphenol, 4-s-butylphenol, 4-s-butenylphenol, 4-(1-propenyl) phenol, 2-allyl-3,4,6-trichlorophenol and 4-allylphenol is alkylated using 1-bromo-7-ethoxy-3,7-dimethyloctane or the mesylate of 7-ethoxy-3,7-dimethyloctan-1-ol according to the processes of Example 1 or 10(D) to yield 7-ethoxy-3,7-dimethyloctyl 2-ethylthiomethylphenyl ether, 7-ethoxy-3,7-dimethyloctyl 4-methylthiomethylphenyl ether, 7-ethoxy-3,7-dimethyloctyl 4-ethylthiomethylphenyl ether, 7-ethoxy-3,7-dimethyloctyl 2-t-butyl-4-methylthiomethylphenyl ether, 7-ethoxy-3,7-dimethyloctyl 2-t-butylthiomethyl-4-ethoxyphenyl ether, 7-ethoxy-3,7-dimethyloctyl 2-t-butylthiomethyl-4-methoxyphenyl ether, 7-ethoxy-3,7-dimethyloctyl 2-allyl-4-chlorophenyl ether, 7-ethoxy-3,7-dimethyloctyl 2-allyl-6-methoxyphenyl ether, 7-ethoxy-3,7-dimethyloctyl 2-allyl-4,6-dinitrophenyl ether, 7-ethoxy-3,7-dimethyloctyl 2-allyl-3,5-dichlorophenyl ether, 7-ethoxy-3,7-dimethyloctyl 4-cyanophenyl ether, 7-ethoxy-3,7-dimethyloctyl 7-n-butoxyphenyl ether, 7-ethoxy-3,7-dimethyloctyl 4-s-butylphenyl ether, 7-ethoxy-3,7-dimethyloctyl 4-(1'-propenyl)phenyl ether, 7-ethoxy-3,7-dimethyloctyl 2-allyl-3,4,6-trichlorophenyl ether and 7-ethoxy-3,7-dimethyloctyl 4-allylphenyl ether.

EXAMPLE 23

Using the process of Example 7, each of 1-(7'-ethoxy-3',7'-dimethyloctyloxy)-4-(methylsulfonylmethyl)benzene and 1-(7'-ethoxy-3',7'-dimethyloctyloxy)-4-(ethylsulfonylmethyl)benzene is prepared from 7-ethoxy-3,7-dimethyloctyl 4-methylthiomethylphenyl ether and 7-ethoxy-3,7-dimethyloctyl 4-ethylthiomethylphenyl ether, respectively.

EXAMPLE 24

Each of 7-methoxy-3,7-dimethyloctyl 4-methylthiophenyl ether, 7-methoxy-3,7-dimethyloct-2-enyl 4-methylthiophenyl ether, 7-ethoxy-3,7-dimethyloctyl 4-methylthiophenyl ether and 7-ethoxy-3,7-dimethyloctyl-2-enyl 4-methylthiophenyl ether is treated with sodium metaperiodate according to the process of Example 6 to yield 7-methoxy-3,7-dimethyloctyl 4-methylsulfinylphenyl ether, 7-methoxy-3,7-dimethyloct-2-enyl 4-methylsulfinylphenyl ether, 7-ethoxy-3,7-dimethyloctyl 4-methylsulfinylphenyl ether and 7-ethoxy-3,7-dimethyloct-2-enyl 4-methylsulfinylphenyl ether, respectively. The corresponding 4-methylsulfonylphenyl ether are prepared using the process of Example 7.

What is claimed is:

1. A compound of the formula:

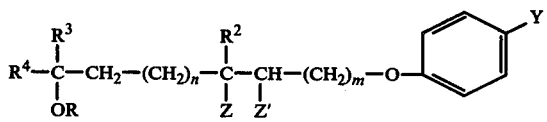

wherein,

Y is lower alkyl or lower alkoxy;

m is the positive integer one or two;

n is the positive integer two or three;

each of $R^2$, $R^3$ and $R^4$ is methyl or ethyl;

R is hydrogen, lower alkyl, cycloalkyl or aralkyl; and each of Z and Z' is hydrogen, or, taken together, a carbon carbon double bond.

2. A compound according to claim 1 wherein m is one; n is two; and Y is lower alkyl.

3. A compound according to claim 2 wherein R is hydrogen or lower alkyl.

4. A compound according to claim 3 wherein Y is ethyl and R is hydrogen, methyl, ethyl or isopropyl.

5. A compound according to claim 4 wherein Z and Z', taken together, form a carbon-carbon bond.

6. A compound according to claim 5 wherein each of $R^2$, $R^3$ and $R^4$ is methyl.

7. The compound, 7-methoxy-3,7-dimethyloct-2-enyl p-ethylphenyl ether, according to claim 6.

8. A compound according to claim 4 wherein each of Z and Z' is hydrogen and each of $R^2$, $R^3$ and $R^4$ is methyl.

9. The compound, 7-ethoxy-3,7-dimethyloct-2-enyl p-ethylphenyl ether.

10. A compound of the formula:

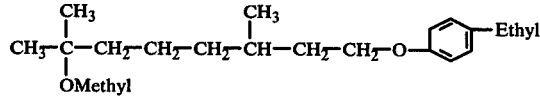

* * * * *